United States Patent [19]
Lukacovic et al.

[11] Patent Number: 5,281,412
[45] Date of Patent: Jan. 25, 1994

[54] ORAL COMPOSITIONS

[75] Inventors: Michael F. Lukacovic, West Chester; Satyanarayana Majeti, Cincinnati, both of Ohio

[73] Assignee: The Procter & Gamble Company, Cincinnati, Ohio

[21] Appl. No.: 31,061

[22] Filed: Mar. 12, 1993

Related U.S. Application Data

[63] Continuation of Ser. No. 814,937, Dec. 30, 1991, abandoned.

[51] Int. Cl.$^5$ .......................... A61K 7/16; A61K 7/18; A61K 33/20
[52] U.S. Cl. ........................................ 424/52; 424/49; 424/53; 424/661; 424/663; 424/665
[58] Field of Search .................. 424/49, 53, 661, 663, 424/665

[56] References Cited

U.S. PATENT DOCUMENTS

| Re. 31,779 | 12/1984 | Alliger | 424/665 |
|---|---|---|---|
| 3,925,543 | 12/1975 | Donohue | 424/52 |
| 3,937,805 | 2/1976 | Harrison | 424/52 |
| 3,937,807 | 2/1976 | Haefele | 424/52 |
| 4,080,441 | 3/1978 | Gaffar et al. | 424/54 |
| 4,104,190 | 8/1978 | Hartshorn | 424/663 |
| 4,118,474 | 10/1978 | Gaffar et al. | 424/54 |
| 4,241,049 | 12/1980 | Colodney et al. | 424/54 |
| 4,256,731 | 3/1981 | Curtis et al. | 424/54 |
| 4,330,531 | 5/1982 | Alliger | 424/53 |
| 4,690,772 | 9/1987 | Tell et al. | 424/665 |
| 4,889,654 | 12/1989 | Mason et al. | 424/661 |
| 4,891,216 | 1/1990 | Kross et al. | 424/661 |
| 4,902,498 | 2/1990 | Agricola et al. | 424/52 |
| 4,986,990 | 1/1991 | Davidson et al. | 424/665 |
| 5,019,402 | 5/1991 | Kross et al. | 424/661 |
| 5,100,652 | 3/1992 | Kross et al. | 424/661 |
| 5,104,660 | 4/1992 | Chvapil et al. | 424/445 |

FOREIGN PATENT DOCUMENTS

| 214540 | 3/1987 | European Pat. Off. | 424/661 |
|---|---|---|---|
| 287074 | 10/1988 | European Pat. Off. | 424/661 |
| 344701 | 12/1989 | European Pat. Off. | 424/661 |
| 8504107 | 9/1985 | PCT Int'l Appl. | |

Primary Examiner—Shep Rose
Attorney, Agent, or Firm—D. C. Mohl; D. K. Dabbiere; J. C. Rasser

[57] ABSTRACT

Oral compositions, such as toothpastes, mouthwashes, lozenges and chewing gum, containing a chlorous acid liberating material and an agent which reduces stain are disclosed herein.

9 Claims, No Drawings

ORAL COMPOSITIONS

This is a continuation of application Ser. No. 814,937 filed Dec. 30, 1991, now abandoned.

TECHNICAL FIELD

The present invention relates to oral compositions containing a chlorous acid liberating material and an agent which reduces stain.

BACKGROUND ART

The use of antimicrobial agents to reduce plaque/gingivitis as well as mouth odor has been recognized for many years. Included among references disclosing oral compositions containing antimicrobials are U.S. Pat. No. 3,937,805, Feb. 10, 1976 to Harrison; U.S. Pat. No. 3,937,807, Feb. 10, 1976 to Haefele; U.S. Pat. No. 4,080,441, Mar. 21, 1978 to Gaffar et al .; U.S. Pat. No. 4,118,474, Oct. 3, 1978 to Gaffar et al.; U.S. Pat. No. 4,241,049, Dec. 23, 1980 to Colodney et al.; U.S. Pat. No. 3,925,543, Dec. 9, 1975 to Donahue; and U.S. Pat. No. 4,256,731, Mar. 17, 1981 to Curtis et al.

In addition to the materials mentioned in the patents set forth above, the prior art discloses the use of chlorine dioxide ($ClO_2$) or chlorous acid ($HClO_2$) liberating materials in oral products. One such reference is German Application 2329753, Dec. 13, 1973, to National Patent Development Corporation. The compositions in this reference are primarily alkaline but they may be acidic.

The German reference and other prior art disclosures which disclose chlorine dioxide or chlorous acid liberating materials in oral products do not suggest that the materials may cause tooth stain or how such stain may optimally be reduced.

The present inventors have discovered that the staining caused by chlorous acid compositions can be reduced by using citrate ions in combination with the chlorous acid and maintaining an appropriate pH.

Tooth stain is believed to be caused by the oxidation of amino acids on proteins (e.g., tryptophan, tyrosine) by chlorous acid, chlorine dioxide (or some other oxychlorine species formed along the chlorous acid/chlorine dioxide pathway) to fom brown-colored oxidation products which bind to the teeth. Citric acid may prevent tooth stain formation by reacting with these oxy chlorine species preventing reaction with amino acids or by preventing the binding of brown colored oxidation products to the tooth enamel . Citrate ions serve two purposes in the present invention: 1) liberation of chlorous acid/chlorine dioxide from the chlorite salt; and 2) prevention of tooth stain formation.

It is an object therefore to provide oral products which are effective against plaque and gingivitis.

It is a further object of the present invention to provide oral products/methods of use which are effective against plaque and gingivitis while not causing significant staining.

It is still a further object of the present invention to provide products utilizing a chlorous acid liberating agent as the active antiplaque-antigingivitis compound and citrate ions as the antistain material.

It is still a further object of the present invention to provide an effective method of treating plaque and gingivitis.

These and additional objectives will become readily apparent from the detailed description which follows.

All percentages and ratios herein are by weight unless otherwise specified. Additionally, all measurements are made at 25° C. unless otherwise specified.

SUMMARY OF THE INVENTION

The present invention embraces oral compositions which provide antiplaque and antigingivitis benefits while also not staining significantly, comprising in one composition:

a) a safe and effective amount of a chlorous acid liberating compound;

b) an amount of a citrate ion source sufficient to lower and buffer the pH of the composition to less than about 6.0 but greater than about 4.0; and c) a pharmaceutically acceptable carrier.

By "safe and effective amount", as used herein, means sufficient compound to reduce plaque/gingivitis or to reduce staining.

By the term "comprising", as used herein, is meant that various additional components can be conjointly employed in the compositions of this invention as long as the active ingredients can perform their intended functions.

By the term "pharmaceutically acceptable carrier", as used herein, is meant a suitable vehicle which can be used to apply the present compositions in the oral cavity.

DETAILED DESCRIPTION OF THE INVENTION

Chlorous Acid Liberating Compound Composition

The present invention employs a chlorous acid liberating compound as one of the components in the compositions. By "chlorous acid liberating compound" is meant any compound which when appropriately treated will liberate chlorous acid. While any chlorous acid liberating compound may be used, water-soluble chlorites are preferred because they are readily available and inexpensive. Typical water-soluble chlorites include alkali metal chlorites and alkaline earth metal chlorites. Sodium chlorite and potassium chlorite are preferred. Sodium chlorite is particularly preferred.

The amount of chlorous acid liberating compound that is used in the present compositions may be generally from about 0.01 to about 10, typically from about 0.10 to about 5.0, and preferably from about 0.20 to about 3.0% by weight of the total composition.

Citrate Ion Source

The citrate ion source used in the present invention is preferably citric acid and/or water soluble salts of citric acid (e.g. sodium citrate and other alkali metal salts). Other protic acids such as tartaric, glycolic, mandelic, salicylic, malic, maleic, lactic, aspartic, phosphoric or other structurally similar acids may be used in combination with citric acid.

The amount of protic acid used should be sufficient to lower the pH of the composition in the range of from about 4.5 to about 6.5, preferably from about 4.5 to about 5.5. Furthermore, this amount may be generally from about 0.01 to about 15, typically from about 0.10 to about 10, and preferably from about 0.5 to about 7.5% by weight of the total composition.

The chlorous acid liberating compound is generally kept separate from the protic acid prior to use in order to avoid premature reaction of the ingredients.

Pharmaceutically Acceptable Carrier

The carrier(s) for chlorous acid liberating compound and the citrate ion material can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

Dentifrices preferably contain from about 0.05% to 10% by weight of the chlorous acid liberating component. Dentifrices also contain an abrasive polishing material and typically also contain sudsing agents, flavoring agents and sweetening agents. Toothpaste compositions additionally contain binders, humectants and water.

The dentifrice abrasive, generally has a particle size of from about 0.1 to about 10 microns in diameter and can be any abrasive polishing material which does not excessively abrade tooth dentin. These include, for example, silica, both precipitated and gels, calcium carbonate, dicalcium orthophosphate dehydrate, calcium pyrophosphate, calcium polymetaphosphate and insoluble sodium polymetaphosphate. Preferably, however, the abrasive is one which has a high degree of compatibility at low pH's with the chlorous acid liberating compounds and fluoride ions. These include, for example silica xerogels such as those described in U.S. Pat. No. 3,538,230 to Pader et al., issued Nov. 3, 1970; hydrofluoric acid-treated amorphous silica abrasives such as those disclosed in U.S. Pat. No. 3,862,307 to DiGiulio, issued Jan. 21, 1975; mineral abrasives coated with cationic polymers such as those disclosed by J. J. Benedict in U.S. Pat. No. 4,157,387, issued Jun. 5, 1979; and condensation products of urea and formaldehyde such as those disclosed in Cooley et al., in U.S. Pat. No. 3,070,510, issued Dec. 24, 1972. All of these patents are incorporated herein by reference.

The total amount of abrasive materials in the dentifrice embodiments of this invention can range from about 0.5% to about 95% by weight of the dentifrice. Preferably toothpastes contain from about 6% to about 60% by weight and toothpowders contain from about 20% to about 95% by weight abrasives.

Dentifrice compositions can also contain emulsifying agents. Suitable emulsifying agents are those which are reasonably stable and foam throughout a wide pH range, including non-soap nonionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide anticaries effectiveness. The fluoride compounds are believed to provide protection against demineralization as well as aid in remineralization of dental enamel. Preferred fluorides are sodium fluoride, stannous fluoride, indium fluoride, and sodium monofluorophosphate. Norris et al., U.S. Pat. No. 2,946,725, issued Jul. 26, 1960 and Widder et al., U.S. Pat. No. 3,678,154, issued Jul. 18, 1972 disclose such salts as well as others, all incorporated herein by reference.

In preparing toothpastes, it is necessary to add some thickening material to provide a desirable consistency. Preferred thickening agents are carboxyvinyl polymers, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols.

The humectant can comprise up to about 65% by weight of the toothpaste composition.

With both humectants and binders, care must be taken if these are combined with the chlorous acid liberating compound that they do not activate the compound before the product is used.

Flavoring agents can also be added to dentifrice compositions. Suitable flavoring agents include oil of wintergreen, oil of peppermint, menthol oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Another preferred embodiment of the present invention is a mouthwash composition. Conventional mouthwash composition components can comprise the carrier for the compositions of the present invention. Mouthwashes generally comprise about 20:1 to about 2:1 of a water/ethyl alcohol solution and preferably other ingredients such as fluoride ion sources, flavor, sweeteners, humectants, and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to about 1.67% fluoride ions (preferably from about 0.0017% to about 0.67%), 0% to 0.3% (preferably 0.03% to 0.3%) flavoring agent, and the balance water. The amount of chlorous acid liberating compound in mouthwashes is typically from about 0.01 to about 0.5% by weight.

Suitable lozenge and chewing gum components are disclosed in U.S. Pat. No. 4,083,955, Apr. 11, 1978 to Grabenstetter et al., incorporated herein by reference.

METHOD OF MANUFACTURE

The carrier compositions of the present invention can be made using methods which are common in the oral products area.

COMPOSITION USE

The present invention in its method aspect involves applying to the oral cavity safe and effective amounts of the compositions. Generally an amount of the composition to provide at least about 50 ppm of chlorous acid is effective.

The following examples further describe and demonstrate preferred embodiments within the scope of the present invention. The examples are given solely for illustration and are not to be construed as limitations of this invention as many variations thereof are possible without departing from the spirit and scope thereof. All of the examples are of dentrifrices and rinses since dentrifrices and rinses are the preferred vehicle and the chlorous acid and protic acid compositions are exemplified first.

EXAMPLE I

Chlorite DUal Phase Dentrifice

| Component | Weight % |
|---|---|
| Chlorite Phase | |
| Sodium Chlorite* | 7.500 |
| Sodium Fluoride | 0.490 |
| Sodium Saccharin | 0.130 |
| Titanium Dioxide | 1.000 |
| Sodium Alkyl Sulfate (28% solution) | 4.000 |
| Silica | 30.000 |
| Xanthan Gum | 0.600 |
| Carbopol | 0.200 |
| NaOH (50% solution) | 1.800 |
| Water | qs to 100 |
| Activator Phase | |
| Sorbitol | 35.435 |
| Sodium Saccharin | 0.150 |
| Sodium Alkyl Sulfate (28% solution) | 4.000 |
| Titanium Dioxide | 0.525 |
| Silica | 22.000 |
| Carboxymethyl Cellulose | 1.300 |
| Sodium Citrate | 10.000 |
| Citric Acid | 5.000 |
| Flavor | 1.100 |
| FD&C Blue Dye | 0.050 |
| Water | qs to 100 |
| Activator Phase pH 4.85 | |
| Final pH of combined phases = 5.0 ± 0.2. | |
| Phases mixed in a 1:1 weight:weight ratio. | |

*Obtained from Olin Chemical (80% purity) chlorite phase pH 10.0.

EXAMPLE II

Chlorite Dual Phase Rinse

| ACTIVATOR PHASE | | CHLORITE PHASE | |
|---|---|---|---|
| Component | Weight % | Component | Weight % |
| Citric acid | 0.30 | NaClO$_2$ | 0.38* |
| Na$_3$ citrate | 0.42 | NaF | 0.10 |
| Glycerin | 20.0 | Water | q.s. |
| Ethanol | 16.00 | | |
| Menthol | 0.025 | | |
| Na saccharin | 0.025 | | |
| D-ribose | 2.00 | | |
| NaH$_2$PO$_4$ | 2.00 | | |
| CaCl$_2$—2H$_2$O | 0.03 | | |
| FD&C Blue #1 | 0.02 | | |
| Water | q.s. | | |

After mixing in 1:1 vol:vol ratio, final pH = 4.5 ± 0.2, final F$^-$ = 225 ppm, and final Ca$^{+2}$ = 40 ppm.

*Obtained from Olin Chemicals (~80% pure).

EXAMPLE III

Chlorite Dual Phase Rinse

| Component | Weight % |
|---|---|
| Activator Phase | |
| Ethanol | 16.000 |
| Menthol | 0.025 |

-continued

| Component | Weight % |
|---|---|
| Sodium Citrate | 0.550 |
| Citric Acid | 0.200 |
| Sodium Saccharin | 0.025 |
| Glycerin | 20.000 |
| FD&C Blue #1 | 0.020 |
| Water | q.s. |
| pH of Activator Phase 5.30. | |
| Chlorite Phase | |
| Sodium Chlorite | 0.38* |
| Sodium Fluoride | 0.10 |
| Water | qs to 100 |
| pH of chlorite phase 11.0 ± 0.2. | |
| Final pH of combined phases 5.50 ± 0.2. | |
| Phases mixed in a 1:1 vol:vol ratio. | |

*Obtained from Olin Chemical (80% purity).

In addition to NaClO$_2$, other alkali metal salts such as KClO$_2$ or LiClO$_2$ or alkaline earth salts such as CaClO$_2$ may be used with similar results being obtained.

What is claimed is:

1. An oral product which provides antiplaque and antigingivitis benefits while also not staining significantly, consisting essentially of:
   (a) from about 0.01 to about 10.0 percent by weight of a metal chlorite based upon the total weight of the chlorite composition;
   (b) a safe and effective amount of a citrate ion source in the citrate ion composition;
   (c) an appropriate flavoring agent;
   (d) pharmaceutically acceptable carriers; and
   wherein the pH of the total composition is from about 5.9 to about 6.5 and wherein the product is substantially free of an antidemineralization agent, and substantially free of lactic acid and wherein said (d) carriers and dual phase, one phase containing component (a) and no component (b), and another phase containing component (b) and no component (a).

2. The composition of claim 1 wherein said composition contains from about 1.0 to about 7.5 percent by weight of a metal chlorite based upon the total weight of the chlorite composition.

3. The composition of claim 2 wherein said composition contains from about 2.5 to about 5.0 percent by weight of a metal chlorite based upon the total weight of the chlorite composition.

4. The composition of claim 1 wherein said composition contains up to about 3.0 percent by weight of a metal chlorite based upon the total weight of the chlorite composition and from about 0.01 to about 15.0 percent by weight of the citrate ions, based upon the total weight of the citrate composition.

5. The composition of claim 4 wherein said composition contains from about 3.0 to about 5.0 percent by weight of metal chlorite based upon the total weight of the chlorite composition.

6. The composition of claim 1 wherein a soluble fluorite ion salt is also included.

7. A method of reducing plaque/gingivitis by applying to the oral cavity of a safe and effective amount of a composition according to claim 1.

8. A method of reducing plaque/gingivitis by applying to the oral cavity a safe and effective amount of a composition according to claim 4.

9. A method of reducing plaque/gingivitis by applying to the oral cavity a safe and effective amount of a composition according to claim 6.

* * * * *

UNITED STATES PATENT AND TRADEMARK OFFICE
CERTIFICATE OF CORRECTION

PATENT NO. : 5,281,412
DATED : January 25, 1994
INVENTOR(S) : Michael Frederick Lukacovic; Satyanarayana Majeti It is certified that error appears in the above-identified patent and that said Letters Patent is hereby corrected as shown below:

<u>Column 6,</u>
Line 33, "4.9 should read -- 5.9 --

Signed and Sealed this

Twenty-eighth Day of August, 2001

*Attest:*

NICHOLAS P. GODICI
*Attesting Officer*     *Acting Director of the United States Patent and Trademark Office*